US009836841B2

(12) United States Patent
Natali et al.

(10) Patent No.: US 9,836,841 B2
(45) Date of Patent: Dec. 5, 2017

(54) SYSTEM AND METHOD FOR PACKAGED MEDICAMENT INSPECTION

(71) Applicants: Luca Natali, Lugo (IT); Fabrizio Golinelli, Corlo di Formigine (IT); Flavio Este, Selvazzano Dentro (IT)

(72) Inventors: Luca Natali, Lugo (IT); Fabrizio Golinelli, Corlo di Formigine (IT); Flavio Este, Selvazzano Dentro (IT)

(73) Assignee: SWISSLOG ITALIA S.P.A., Milan (IT)

( * ) Notice: Subject to any disclaimer, the term of this patent is extended or adjusted under 35 U.S.C. 154(b) by 0 days.

(21) Appl. No.: 14/934,939

(22) Filed: Nov. 6, 2015

(65) Prior Publication Data
US 2016/0292858 A1  Oct. 6, 2016

Related U.S. Application Data

(63) Continuation of application No. 13/983,445, filed as application No. PCT/IB2011/052053 on May 10, 2011, now abandoned.
(Continued)

(51) Int. Cl.
*G06K 9/00* (2006.01)
*G06T 7/00* (2017.01)
(Continued)

(52) U.S. Cl.
CPC ....... *G06T 7/0014* (2013.01); *G01N 21/9508* (2013.01); *G01N 33/15* (2013.01); *G06K 9/6202* (2013.01); *G06T 2207/10152* (2013.01)

(58) Field of Classification Search
USPC ............. 356/237.1; 382/110, 141, 143, 218; 700/242
See application file for complete search history.

(56) References Cited

U.S. PATENT DOCUMENTS 5,363,968 A  11/1994 Soloman
5,502,944 A * 4/1996 Kraft .................. G07F 17/0092
221/2
(Continued)

FOREIGN PATENT DOCUMENTS

EP  2 082 963 A1  7/2009
EP  2 175 230 A1  4/2010
(Continued)

OTHER PUBLICATIONS

Kim, J., "Medicine packet inspecting apparatus," EP 2175230 A1, Apr. 14, 2010.*
(Continued)

*Primary Examiner* — Xuemei Chen
(74) *Attorney, Agent, or Firm* — Flynn, Thiel, Boutell & Tanis, P.C.

(57) ABSTRACT

A unit-dose medicament inspection system and method provide for the obtainment of an image of a receptacle after a corresponding filling operation in which a predetermined unit-dose medicament was to have been located in the receptacle. The image may be processed to extract image data that may be compared with stored data corresponding with a predetermined unit-dose medicament. Size, configuration and other features of objects located within a receptacle may be included with the extracted image data and compared with corresponding stored data to determine whether a given receptacle includes the intended medicament and/or whether the medicament located within the receptacle is an acceptable condition. Receptacle attributes may also be inspected for compliance with predetermined configuration parameters.

21 Claims, 10 Drawing Sheets

Related U.S. Application Data

(60) Provisional application No. 61/439,321, filed on Feb. 3, 2011.

(51) Int. Cl.
  *G01N 21/95* (2006.01)
  *G01N 33/15* (2006.01)
  *G06K 9/62* (2006.01)

(56) References Cited

U.S. PATENT DOCUMENTS

| | | | |
|---|---|---|---|
| 5,926,556 A * | 7/1999 | Douglas | G06K 7/10722 250/223 B |
| 6,330,351 B1 * | 12/2001 | Yasunaga | G01N 21/9508 382/141 |
| 6,601,729 B1 | 8/2003 | Papp | |
| 6,738,723 B2 * | 5/2004 | Hamilton | A61J 7/02 137/2 |
| 6,894,772 B2 * | 5/2005 | Goetz | B07C 5/342 356/237.1 |
| 7,210,598 B2 | 5/2007 | Gerold et al. | |
| 7,584,018 B2 | 9/2009 | Shows et al. | |
| 7,792,349 B2 | 9/2010 | Van Den Brink | |
| 7,796,799 B2 | 9/2010 | Jorritsma | |
| 7,894,656 B2 | 2/2011 | Kim | |
| 8,041,102 B2 * | 10/2011 | Yuyama | G07F 11/44 382/143 |
| 8,121,392 B2 | 2/2012 | Popovich et al. | |
| 8,340,392 B2 | 12/2012 | Kim | |
| 8,345,989 B1 * | 1/2013 | Bresolin | G06K 9/00 382/218 |
| 8,380,346 B2 * | 2/2013 | Chudy | G06F 19/3462 700/242 |
| 8,457,361 B2 * | 6/2013 | Julius | G01N 21/9508 382/110 |
| 8,477,989 B2 | 7/2013 | Bresolin | |
| 8,584,715 B2 | 11/2013 | Stoeckel et al. | |
| 8,670,066 B2 | 3/2014 | Newcomb et al. | |
| 8,712,163 B1 | 4/2014 | Osheroff | |
| 8,727,208 B2 * | 5/2014 | Poisner | G06K 19/06046 235/375 |
| 8,773,660 B2 | 7/2014 | Pommereau et al. | |
| 2007/0000939 A1 * | 1/2007 | Vasiadis | B65G 47/1457 221/264 |
| 2008/0047969 A1 * | 2/2008 | Farhan | G07F 9/026 221/7 |
| 2011/0282488 A1 | 11/2011 | Horev et al. | |
| 2013/0170732 A1 | 7/2013 | Gotou et al. | |
| 2013/0188038 A1 | 7/2013 | Tanimoto et al. | |

FOREIGN PATENT DOCUMENTS

| | | |
|---|---|---|
| JP | 2007-503044 A | 2/2007 |
| WO | WO 02/25568 A2 | 3/2002 |
| WO | WO 2005/017814 A1 | 2/2005 |

OTHER PUBLICATIONS

Form PCT/ISA/220 dated Oct. 31, 2011 (1 page).
Form PCT/ISA/210 dated Oct. 31, 2011 (4 pages).
Form PCT/ISA/237 dated Oct. 31, 2011 (5 pages).
Remarks submitted with Amendment under Article 34 PCT dated Feb. 4, 2013 in Application No. PCT/IB2011/052053 (1 page).
Form PCT/IPEA/416 mailed Jun. 18, 2013 (1 page).
Form PCT/IPEA/409 mailed Jun. 18, 2013 (9 pages).
Office Action issued in Korean Application No. 10-2013-7023323, with English translation, dated Dec. 8, 2016 (16 pages).

* cited by examiner

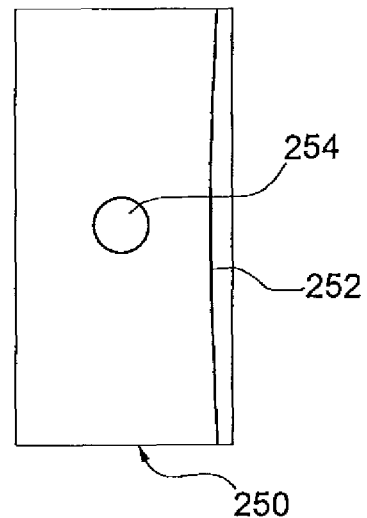
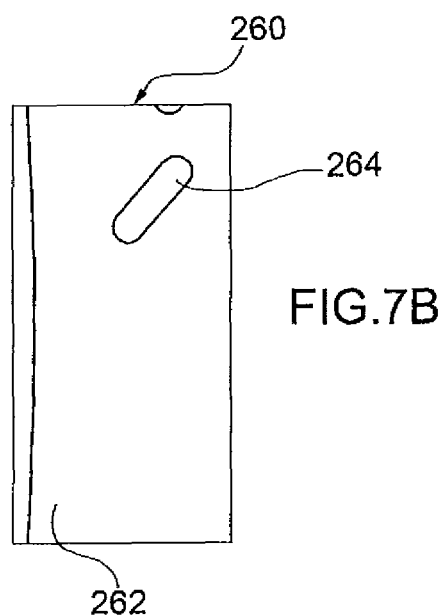
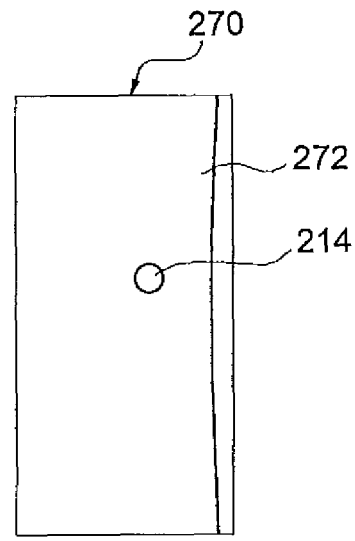

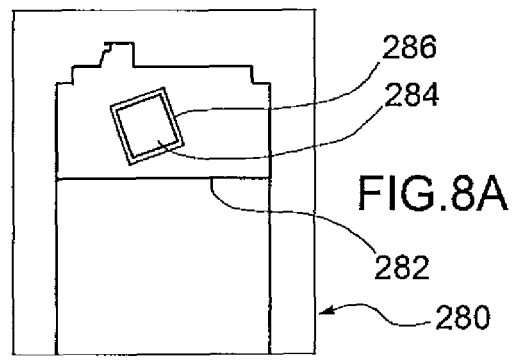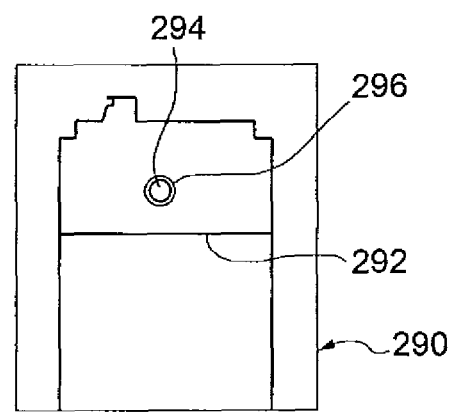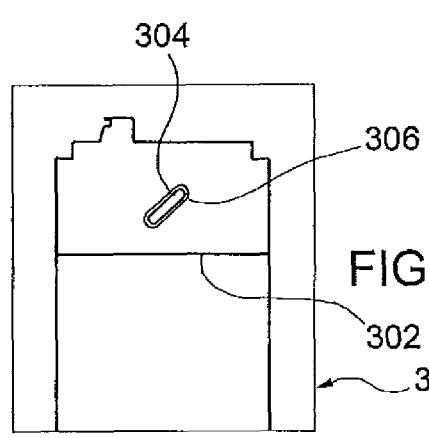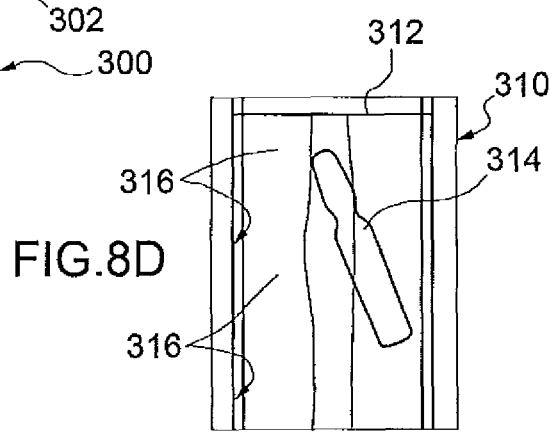

SYSTEM AND METHOD FOR PACKAGED MEDICAMENT INSPECTION

CROSS REFERENCE TO RELATED APPLICATIONS

This is a continuation of prior U.S. application Ser. No. 13/983,445, filed Aug. 2, 2013, which is the national stage of International Application No. PCT/IB2011/052053, filed May 10, 2011, which claims the benefit of U.S. Provisional Application No. 61/439,321, filed Feb. 3, 2011.

FIELD OF THE INVENTION

The present invention relates to the inspection of receptacles, or packages, for unit-dose medicaments. The invention is particularly apt for automated inspection implementations.

BACKGROUND OF THE INVENTION

Unit-dose packaging approaches are being utilized in medical care facilities to provide predetermined unit-dose medicaments. By way of example, unit-dose packaging systems may be implemented within a medical dispensary (e.g., a pharmacy) located at a hospital or other patient care facility, wherein the medical dispensary packages a unit-dose medicament in a sealed package for distribution within the medical facility and administration to a patient located at the medical facility. In conjunction with such systems, the accuracy, integrity and reliability of packaged contents is a primary concern. Further, the efficiencies associated with such packaging is of particular interest.

Despite numerous advances made to date, the present inventors have recognized the desirability of providing an improved system and method for packaged unit-dose medicament inspection, wherein packaged contents may be inspected in conjunction with packaging operations to improve the accuracy, integrity and reliability of packaging and overall packaging efficiencies.

SUMMARY OF THE INVENTION

An improved system and method for handling and inspecting receptacles containing corresponding predetermined unit-dose medicaments is provided. By way of example, such "predetermined unit-dose medicaments" may be in the form of pills, tablets, capsules, blister packs (e.g. hand-cut or automated, machine cut), vials, or any other configuration or packaging utilized for a single dose of a given medicament to be administered to a patient.

In one embodiment, a system for handling a given unit-dose receptacle may include at least a first imaging device for obtaining at least one image of the given receptacle and providing a first output signal corresponding therewith. The system embodiment may further include a processor (e.g. a digital signal computer processor) operable for processing the first output signal to extract corresponding first image data and for comparing the first image data with stored data. For a given receptacle, the stored data may correspond with at least one of a predetermined attribute of the corresponding, predetermined unit-dose medicament and/or a predetermined attribute of the given receptacle.

Inspection of a given receptacle after the intended filling of such receptacle with a corresponding predetermined unit-dose medicament may yield a number of advantages. For example, post-filling inspection allows for the identification of instances where a given receptacle fails to include the intended unit-dose medicament and/or the correct dosage of the medicament and/or where the packaged medicament is in a damaged condition. Further, such inspection allows receptacles having identified configuration discrepancies to be identified. For example, receptacles having edge seals and/or apertures (e.g., for hanging the receptacles) that vary from a predetermined standard may be readily identified. In turn, non-compliant receptacles may be handled accordingly and/or corresponding production equipment may be serviced.

In one approach, the first imaging device may include an imaging signal source for providing an imaging signal (e.g. an electromagnetic radiation signal such as a visible and/or infrared light signal), and an imaging signal detector for detecting at least a portion of the imaging signal and providing the first output signal. In one approach, the imaging signal source may be positioned on and illuminate a first side of the receptacle and the imaging signal detector may be positioned on a second side of the receptacle to receive portions of the imaging signal passing through the receptacle which are not otherwise blocked by the contents of the receptacle (e.g., a "back-light" approach). In another approach, the imaging signal source may be positioned on and illuminate a first side of the receptacle and the imaging signal detector may also be positioned on the first side of the receptacle (e.g., a "front-light" approach). In either approach, a digital camera may be employed as the imaging signal detector, wherein the digital camera may provide the output signal in a digital form to the processor.

As noted, the processor may be operable to extract first image data in relation to each given receptacle. In some embodiments, such first image data may comprise one or more of a contents-related group consisting of: data relating to a presence of an object within the given receptacle; data relating to a number of objects within the given receptacle; data relating to a shape, or pattern, of an object within the given receptacle; and data relating to a size (e.g. a measurable physical parameter) of an object within the given receptacle. In this regard, the processor may utilize stored software algorithms and/or other processing logic to extract the first image data, including for example edge-detection software algorithms, corner/interest point detection software algorithms; and/or blob detection software algorithms.

In various embodiments, the system may further include a database for storing data corresponding with at least one predetermined medicament attribute of the predetermined unit-dose medicament corresponding with a given receptacle, such attribute being one or more of a first predetermined group consisting of: a predetermined number of physically discrete units comprising the corresponding predetermined unit-dose medicament (e.g., typically one (1)); a predetermined shape, or pattern, of each physically discrete unit comprising the corresponding predetermined unit-dose medicament (e.g., circular, rectangular, oval etc.); and a predetermined size of each physically discrete unit comprising the corresponding predetermined unit-dose medicament (e.g., as reflected by measured cross-dimensions, perimeter, area, etc.). Such stored data may be previously input into the system based upon measured, statistically-established parameters and/or otherwise pre-established, acceptable patterns, corresponding with each given predetermined unit-dose medicament. For each attribute, the stored data may comprise a predetermined range of acceptability, e.g. established based on appropriate input and/or empirical data.

As may be appreciated, comparison of extracted contents-related image data with corresponding stored medicament-related data allows the inspection system to identify instances in which a given package fails to include the intended predetermined medicament (e.g., as reflected by a size or shape that does not correspond to the intended unit does medicament) and/or the proper unit-dose of such medicament (e.g., to many separate pills) and/or in which the packaged medicament is in an unacceptable damaged condition (e.g. fractured pills, broken vials, etc.).

In some embodiments, for each given receptacle, the processor may be operable to extract first image data that may comprise at least one of a receptacle-related group consisting of: data relating to a shape of a predetermined sealed region of the given receptacle; data relating to a shape of a predetermined edge portion of the given receptacle; and data relating to a light transmissivity of a predetermined region of the given receptacle. In such embodiments, the processor may utilize corresponding stored software algorithms and/or other processing logic to extract the first image data, including for example edge-detection software algorithms, core-interest point detection software algorithms, interest point detection software algorithms, and/or blob-detection software algorithms.

In conjunction with such embodiments, the system may include a database for storing data corresponding with at least one predetermined attribute of the given receptacle, such attribute being one or more of a second predetermined group consisting of: a predetermined shape of the predetermined sealed region of the given receptacle; a predetermined shape of the predetermined edge portion of the given receptacle; and a predetermined light transmissivity of the predetermined region of the given receptacle. As may be appreciated, comparison of extracted receptacle-related image data with stored receptacle data allows the inspection system to identify instances in which a given receptacle has a configuration and/or seal condition of concern. For example, peripheral and aperture edges may be identified that indicate a potential receptacle condition of concern and/or which otherwise indicate that corresponding production equipment may be in need of maintenance, etc. For each attribute, the stored data may comprise a predetermined range of acceptability, e.g. established based on appropriate input and/or empirical data.

In some implementations, the system may include at least a second imaging device for obtaining at least another image of the receptacle and providing a second output signal corresponding therewith, wherein the processor is operable to process the second output signal to extract the second image data. In such arrangements, the processor may be operable for comparing the first image data with stored data corresponding with at least one predetermined attribute of the unit-dose medicament, and the same or another processor may be operable for comparing the second image data with stored data corresponding with at least one predetermined attribute of the receptacle. In this regard, the first image data may correspond with at least one of a contents-related group as noted above, and the second image data may correspond with at least one of a receptacle-related group as noted above.

In one approach, the processor may be operable to output an alert signal when comparison operations by the processor indicate that the presence of a predetermined condition. By way of example, such predetermined condition may be one corresponding with potential concern regarding whether the intended content (e.g., unit-dose medicament) is present and/or whether the content is in an appropriate condition. Additionally and/or alternatively, such predetermined condition may correspond with a potential concern regarding the size, configuration and/or condition of a given receptacle.

The alert signal may be in the form of an audible and/or visible output at a user interface. The system may be operable to allow a user to selectively view the image(s) corresponding with the given receptacle having the predetermined condition and/or one or more image(s) of an acceptable configuration corresponding with the intended unit dose medicament of the given receptacle.

In various implementations, the system may comprise automated componentry as will be further discussed. Further, the system may be networked with additional computer databases comprising stored medicament-related data.

As may be appreciated, an inventive method is also provided. The method is employable in handling one or a plurality of receptacles for separately containing a corresponding unit-dose medicament. For each given receptacle, the method may include obtaining at least one separate image of the receptacle, and processing the image to extract corresponding image data. In turn, for a given receptacle the method may further include the step of comparing the extracted image data with stored data. The extracted image data and stored data may correspond with a predetermined attribute of the corresponding unit-dose medicament and/or of the given receptacle. As may be appreciated, comparison of image data after intended filling of a given receptacle with a corresponding unit-dose medicament provides reliability and handling advantages.

The predetermined medicament attribute data corresponding with a given unit-dose medicament may comprise: a predetermined number of physically discrete units comprising the corresponding predetermined unit-dose medicament (e.g., typically one (1)); a predetermined shape, or pattern, of each physically discrete unit comprising the corresponding predetermined unit-dose medicament (e.g., circular, rectangular, oval etc.); and/or a predetermined size of each physically discrete unit comprising the corresponding predetermined unit-dose medicament (e.g., as reflected by cross-dimensions, perimeter, area, etc).

In this regard, and in another aspect, an inventive method may be provided for generating predetermined attribute data corresponding with one or a plurality of unit-dose medicaments for use in an inspection system. For example, such method may be employed in conjunction with a method for inspecting a plurality of receptacles for separately contained different corresponding ones of a plurality of unit-dose medicaments.

In conjunction with the generation of predetermined attribute data for a given unit-dose medicament, the method may include the steps of obtaining at least a first image for each of a corresponding plurality of medicament test samples, and extracting test image data from the images. In turn, each of the plurality of test samples may be inspected to identify acceptable ones. For example, such inspection may be manually completed by an operator of the process and/or in an automated manner (e.g. utilizing one or more software algorithms). The method may further include using the test image data corresponding with acceptable ones of the plurality of test samples to generate the predetermined attribute data for the given unit-dose medicament.

In some embodiments, the predetermined attribute data for one or each of a plurality of unit-dose medicaments may comprise corresponding pattern data indicative of at least one acceptable shape. In certain implementations the predetermined attribute data for one or each of a plurality unit-dose medicaments may comprise corresponding pattern data indicative of a plurality of acceptable shapes.

In some embodiments, for one or each of a plurality of unit-dose medicaments the predetermined attribute data may comprise corresponding size, or physical attribute, data corresponding with an acceptable one or more physical parameters (e.g., as reflected by cross-dimensions (e.g. length, width and/or thickness), perimeter, area, etc). In certain implementations, for one or each of a plurality of unit-dose medicaments the predetermined attribute, data may comprise corresponding size, or physical attribute data corresponding with a plurality of acceptable physical parameters.

In some implementations, the method may include the step of sealably closing a given receptacle prior to the obtainment of the corresponding separate image(s) of such receptacle. In this regard, such closing step may be completed after intended filling of a given receptacle with the corresponding intended unit-dose medicament.

In conjunction with the method embodiment, the obtainment of an image(s) may include the steps of illuminating one side of a given receptacle (e.g., via an imaging signal provided by an electromagnetic radiation source). In turn, the image(s) may be captured on another side of the given receptacle during a portion of the illuminating step (e.g., a "back-light" approach) and/or on the same side during a portion of the illuminating step (e.g., a "front-light" approach). In either approach, the image(s) may be captured by an imaging signal detector (e.g., a digital camera), wherein features of the receptacle and/or contents of the receptacle may be extracted from the image(s).

The extracted image data may comprise one or more of a contents-related group consisting of: data relating to a presence of an object within the given receptacle; data relating to a number of objects within the given receptacle; data relating to a shape of an object within the given receptacle; and data relating to a size of an object within the given receptacle. In turn, the comparing step for a given receptacle may include a comparison of the corresponding image data to stored data corresponding with at least one predetermined attribute of the corresponding predetermined unit-dose medicament. As noted, the at least one predetermined medicament attribute may be one of a first predetermined group consisting of: a predetermined number of physically discrete units comprising the corresponding unit-dose medicament (e.g., typically one (1)); a predetermined shape of each physically discrete unit comprising the corresponding unit-dose medicament; and a predetermined size of each physically discrete unit comprising the corresponding predetermined one of said plurality of unit-dose medicament.

Additionally and/or alternatively, the extracted image data for a given receptacle may comprise at least one of a receptacle-related group consisting of: data relating to a shape of a predetermined sealed region the given receptacle; data relating to a shape of a predetermined edge portion of the given receptacle; and data relating to a light transmissivity of a predetermined region of the given receptacle. In turn, the comparing step for a given receptacle may include a comparison of the extracted image data to stored data corresponding with at least one predetermined attribute of the given receptacle. The at least one predetermined receptacle attribute may be one of a second predetermined group consisting of: a predetermined shape of the predetermined sealed region of the given receptacle; a predetermined shape of the predetermined edge portion of the given receptacle; and a predetermined light transmissivity of the predetermined region of the given receptacle.

In certain embodiments, for a given receptacle, image obtainment may entail obtainment of at least a first image (e.g., for processing to extract the image data corresponding with at least one predetermined medicament attribute), and obtainment of at least a second image (e.g. for processing to extract image data corresponding with at least one predetermined receptacle attribute). In various approaches, a first image and a second image may be obtained at the same location or at different locations.

In some embodiments, the method may include a comparison step that provides for the identification of a given receptacle as being non-compliant when a discrepancy between image data and corresponding stored data exceeds a predetermined range. For example, in relation to a given extracted medicament-related attribute or receptacle-related attribute a comparison to the corresponding stored attribute may be conducted in a manner such that a given receptacle is only identified as being non-compliant if the comparison identifies a difference that exceeds a predetermined amount, magnitude, or variance.

In instances when a given receptacle is identified as non-compliant, embodiments may provide an output signal that causes the given receptacle to be discarded. For example, in automated implementations the receptacle may be automatically removed from production processing and a new receptacle may be utilized for the corresponding predetermined medicament.

Additionally and/or alternatively, when a given receptacle is identified as non-compliant, certain embodiments may provide an alert signal to a user (e.g., an audible and/or visible signal). In turn, the user may selectively determine an appropriate remedial action.

In some applications, the method may be provided to allow a user to selectively access and view the image(s) obtained with respect to a given receptacle identified as non-compliant. In turn, a user may take remedial action.

In various applications, a method embodiment may provide for locating a given receptacle at a predetermined fill location for intended receipt of the corresponding predetermined unit-dose medicament. In turn, a fill operation may initiate for the given receptacle. In some approaches, the method embodiment may further include closing a given receptacle after the receptacle has been located and the fill operation initiated. The closing step may be completed prior to or after the obtainment of one or more inspection images of the receptacle.

In various applications, one or more of the noted method embodiment steps may be completed in an automated fashion. Further, certain embodiments may provide for automated movement of a given receptacle between a plurality of different work stations, e.g., for filling, inspection imaging, etc. In this regard, the method is particularly apt for automated implementations in which a plurality of receptacles are automatically filled with corresponding predetermined unit-dose medicaments, that may be the same or different, and inspected for contents verification and receptacle integrity. Numerous additional features and advantages of the present invention will become apparent to those skilled in the art upon consideration of the embodiment descriptions provided hereinbelow.

BRIEF DESCRIPTION OF THE DRAWINGS

FIGS. 7A, 7B and 7C illustrate additional images obtainable for inspection use in various embodiments.

FIGS. 8A, 8B, 8C and 8D illustrate further images obtainable for inspection use in various embodiments.

DETAILED DESCRIPTION

Figure 1:
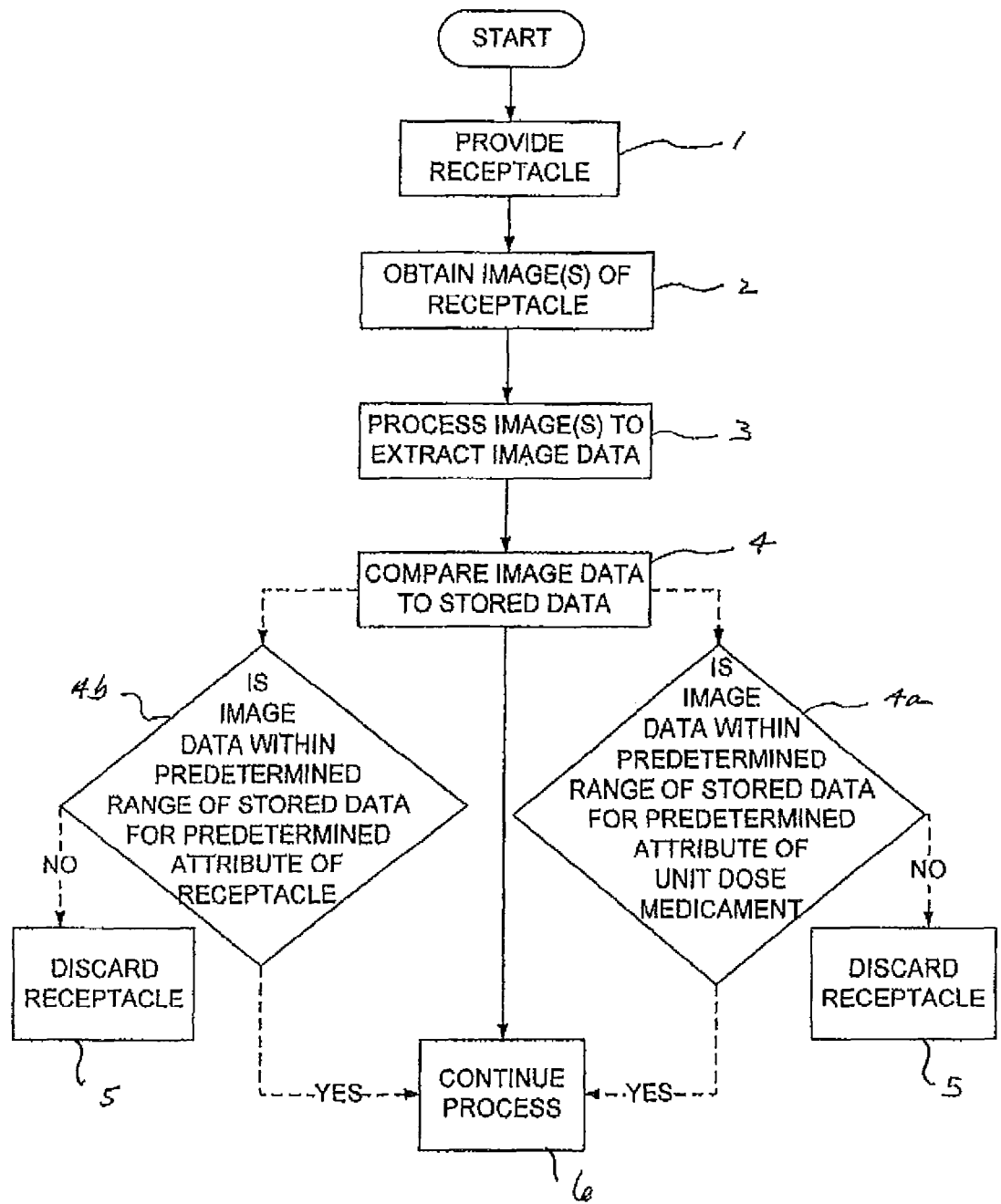
FIG. 1 illustrates one embodiment of a method for inspecting receptacles for containing predetermined unit-dose medicaments.

FIG. 1 illustrates one embodiment of a method for inspecting receptacles for containing corresponding predetermined unit-dose medicaments. Such embodiment may be employed in a variety of settings, including production facilities and medicament dispensaries. In the later regard, single-dose medicament dispensaries may be located at hospitals and other medical care facilities.

Increasingly, such dispensaries are at least partially automated and the illustrated embodiment is particularly apt for automated implementation.

The embodiment of FIG. 1 includes an initial step of providing a receptacle for receiving a given unit-dose medicament (step 1). By way of primary example, such receptacle may be provided after handling at a package filling station at which a predetermined unit-dose medicament was located or was intended to have been located therewithin.

In primary implementations, a given receptacle may be provided in a closed condition (e.g., sealably closed). In other implementations, the receptacle may be provided with an open port.

As shown in FIG. 1, the method embodiment includes the step of obtaining one or more image(s) of the receptacle (step 2). In this regard, image(s) may be obtained in a manner so that predetermined attributes of objects contained within and/or predetermined attributes of the receptacle may be ascertained. For such purposes, an imaging signal source and detector may be disposed on the same side or opposite sides of a receptacle, wherein the material comprising the receptacle may be selected to be at least partially transmissive in relation to the type of imaging signal employed (e.g., transmissive to electromagnetic radiation). By way of example, the imaging signal detector may comprise a camera that provides a digital output signal.

Following image acquisition, the embodiment includes processing the image(s) to extract image data (step 3). In this regard, image processing may entail processing a digital image signal to detect features and extract image data regarding such features, e.g., utilizing a computer processor and software algorithms. In particular, image data may be extracted that is indicative of the presence of and/or one or more physical attributes of contents (e.g., objects) located within the receptacle and/or indicative of one or more physical attributes of the receptacle. For such purposes, one or more of the following types of software algorithms may be employed: edge-detection software algorithms; corner/interest point detection software algorithms; and/or blob detection software algorithms.

Extracted image data that may be indicative of a physical attribute of the content of a receptacle may include: data relating to a presence of an object within the given receptacle; data relating to a number of objects within the given receptacle; data relating to a shape, or pattern, of an object within the given receptacle; and, data relating to a size of an object within the given receptacle (e.g. a measurable physical parameter such as a length, width, thickness, perimeter, area, etc.). Extracted image data that may be indicative of one or more physical attributes of a receptacle may include: data relating to a shape of a predetermined sealed region of the given receptacle; data relating to a shape of a predetermined edge portion of the given receptacle; and data relating to a light transmissivity of a predetermined region of the given receptacle.

The method embodiment may further provide for a comparison of the extracted image data to stored data (step 4). Again, such comparison may be carried out by a computer processor and associated software.

The stored data may be indicative of one or more predetermined physical attributes of the corresponding unit-dose medicament that was located within or intended for location within the given receptacle. By way of example, such predetermined medicament attribute may correspond with one or more of the following: a predetermined shape, or pattern, of the given unit-dose medicament; a predetermined physical parameter, or size, of the given unit-dose medicament (e.g. a measurable physical parameter such as a length, width, thickness, perimeter, area, etc.); a predetermined number of physically discrete units corresponding with the given unit-dose medicament (e.g., typically one).

In turn, a comparison may be completed to determine whether extracted image data corresponding with a physical attribute(s) of any detected object within the receptacle is within a predetermined range of, or variance relative to, a corresponding acceptable predetermined physical attribute of the corresponding unit-dose medicament (step 4a). Such predetermined range may be established to provide a high degree of unit-dose medicament inspection reliability, while reducing instances of false failed inspections (e.g., instances in which an acceptable packaged unit-dose medicament fails inspection).

Stored data may also be indicative of one or more predetermined physical attributes of an acceptably configured, and preferably sealably-closed, receptacle corresponding with a given unit-dose medicament. By way of example, such predetermined receptacle attribute may correspond with one or more of the following: a predetermined shape of said predetermined sealed region of said given one of said plurality of receptacles; a predetermined shape of said predetermined edge portion of said given one of said plurality of receptacles (e.g., a peripheral edge or aperture edge); and, a predetermined light transmissivity of said predetermined region of said given one of said plurality of receptacles.

In turn, a comparison may also be completed to determine whether extracted image data corresponding with a physical attribute of the corresponding receptacle is within a predetermined range corresponding with such physical attribute (step 4b). Again, a predetermined range may be established to provide a high degree of receptacle inspection reliability, while reducing instances of false failed inspections (e.g., instances in which an acceptable receptacle fails inspection).

In instances where a given inspection comparison is outside of a corresponding predetermined range (e.g., pursuant to step 4*a* and/or step 4*b* above), the corresponding receptacle may be discarded (step 5). By way of example, the corresponding receptacle may be automatically diverted from an automated material handling system. Additionally and/or alternatively, an alert signal may be provided to a user.

When a given receptacle passes all corresponding inspection comparisons, the receptacle may be provided for further handling (step 6). By way of example, such receptacle may be automatically transported to a predetermined location for storage and/or dispensation to medical personnel for administration to a patient.

The embodiment of FIG. 1 may be implemented in conjunction with additional method steps in an embodiment for packaging and inspecting unit-dose medicaments. In this regard, reference is now made to FIG. 2 which illustrates process steps that may be completed prior to the method embodiment steps of FIG. 1. As shown, a desired unit-dose medicament may be specified for packaging in an initial step (step 10). By way of example, a desired unit-dose medicament may be specified via a user interface and a computer database associated with the system.

Figure 2:
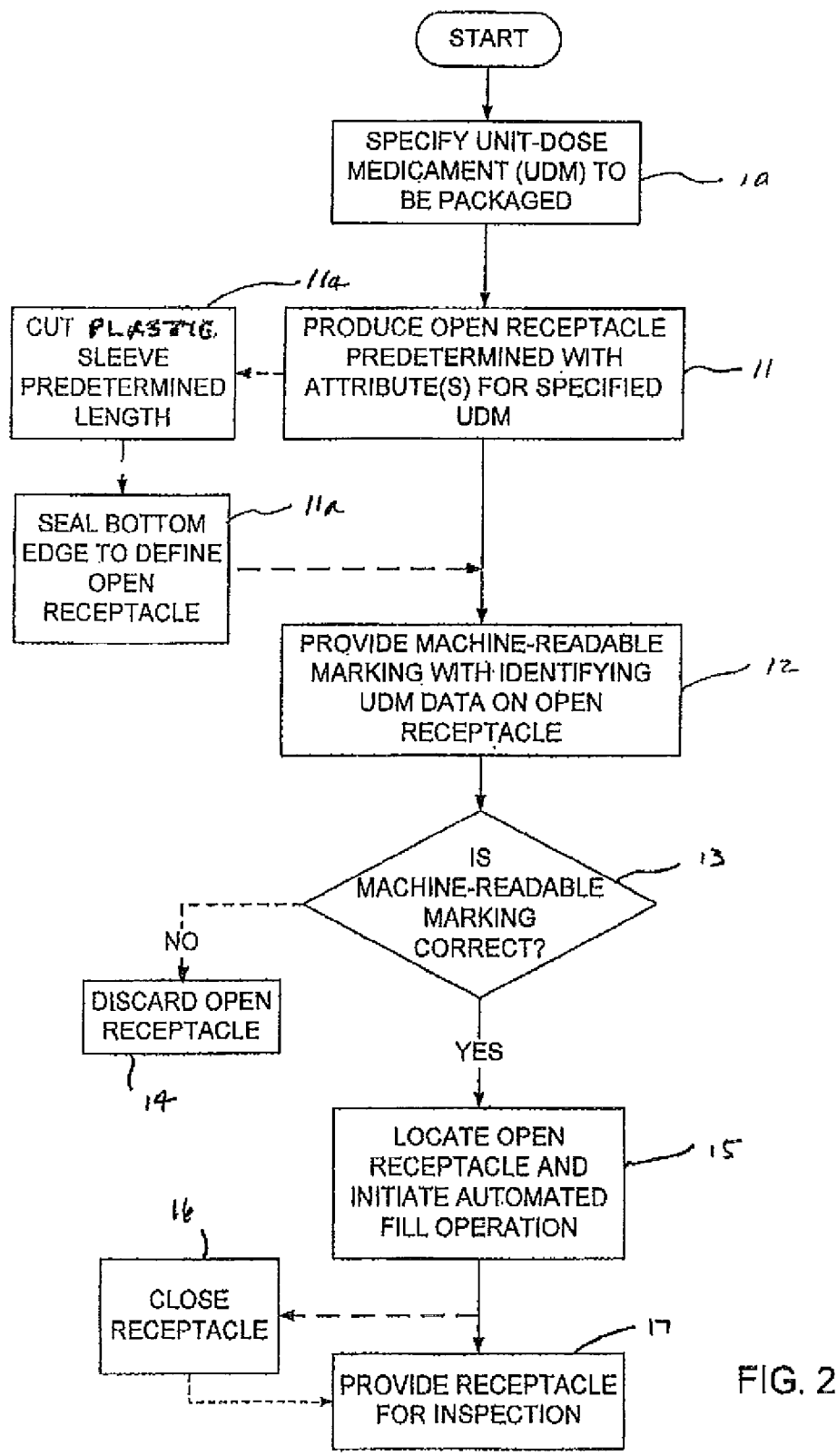
FIG. 2 illustrates a process embodiment employable in conjunction with the embodiment of FIG. 1.

Next, an open port receptacle may be produced for receipt of the specified unit-dose medicament (step 11). In this regard, a computer database may be accessed that comprises data corresponding with an appropriate predetermined receptacle for receiving the specified unit-dose medicament. By way of example, the computer database may comprise information regarding the size, configuration and/or other attributes of an appropriate predetermined receptacle for receiving the specified unit-dose medicament. As shown in FIG. 2, an open port receptacle having the above-noted predetermined attributes may then be produced for receipt of the specified unit-dose medicament.

By way of example, in arrangements adapted for packaging utilizing flexible polymer-based receptacles, cylindrical sleeves of plastic may be utilized to define disposable plastic bag-like receptacles of a predetermined configuration (step 11*a*). By way of example, one or more reels of plastic sleeves having corresponding predetermined diameters may be cut to one or more predetermined lengths to define cylindrical sleeve sections of predetermined volume. In turn, a bottom edge of each cut sleeve section may be sealed (e.g., by welding) (step 11*b*). Upon such bottom edge sealing, an open port receptacle may be defined.

After or prior to such open port receptacle production, a machine-readable marking may be provided that comprises data that identifies a given unit-dose medicament to be located within a given receptacle (step 12), e.g. a machine-readable marking that identifies a unit-dose medicament by pharmaceutical description, source, dosage, etc. By way of example, a machine-readable marking (e.g., a barcode) may be located (e.g., printed) on a predetermined portion of a cylindrical sleeve to be cut or previously cut (e.g., either before or after bottom edge sealing).

The presence and accuracy of the machine-readable marking may be verified for each given receptacle. By way of example, a wireless reader may be positioned relative to the corresponding cylindrical sleeve portion for a given receptacle and utilized to provide an output signal indicative of any machine-readable data provided on the predetermined portion of such cylindrical sleeve. In turn, the data read from the predetermined portion may be compared with stored data indicative of the intended, given unit-dose medicament to be located within the receptacle. Further, a signal may be provided to reinitiate the provision, filling and inspection of another receptacle for the corresponding predetermined unit-dose medicament.

In the event that such comparison fails to indicate a match, the corresponding receptacle may be discarded. In the event a match is indicated, the corresponding receptacle may be located for filling with the intended unit-dose medicament. In turn, and by way of example, the filling of the given receptacle may be completed in an automated fashion. In an automated filling approach, the open port of a given receptacle may be disposed for receipt of the corresponding unit-dose medicament therewithin. In turn, an insertion device may be utilized to automatically insert the corresponding unit-dose medicament into the receptacle.

Upon filling a given receptacle, the receptacle may be closed. By way of example, after location at a filling station and initiation of a filling operation a given receptacle may be automatically sealed at its open port (e.g., via welding). In turn, upon closure of a given receptacle, the receptacle may be provided for inspection, such as that described hereinabove in relation to FIG. 1.

Figure 3:
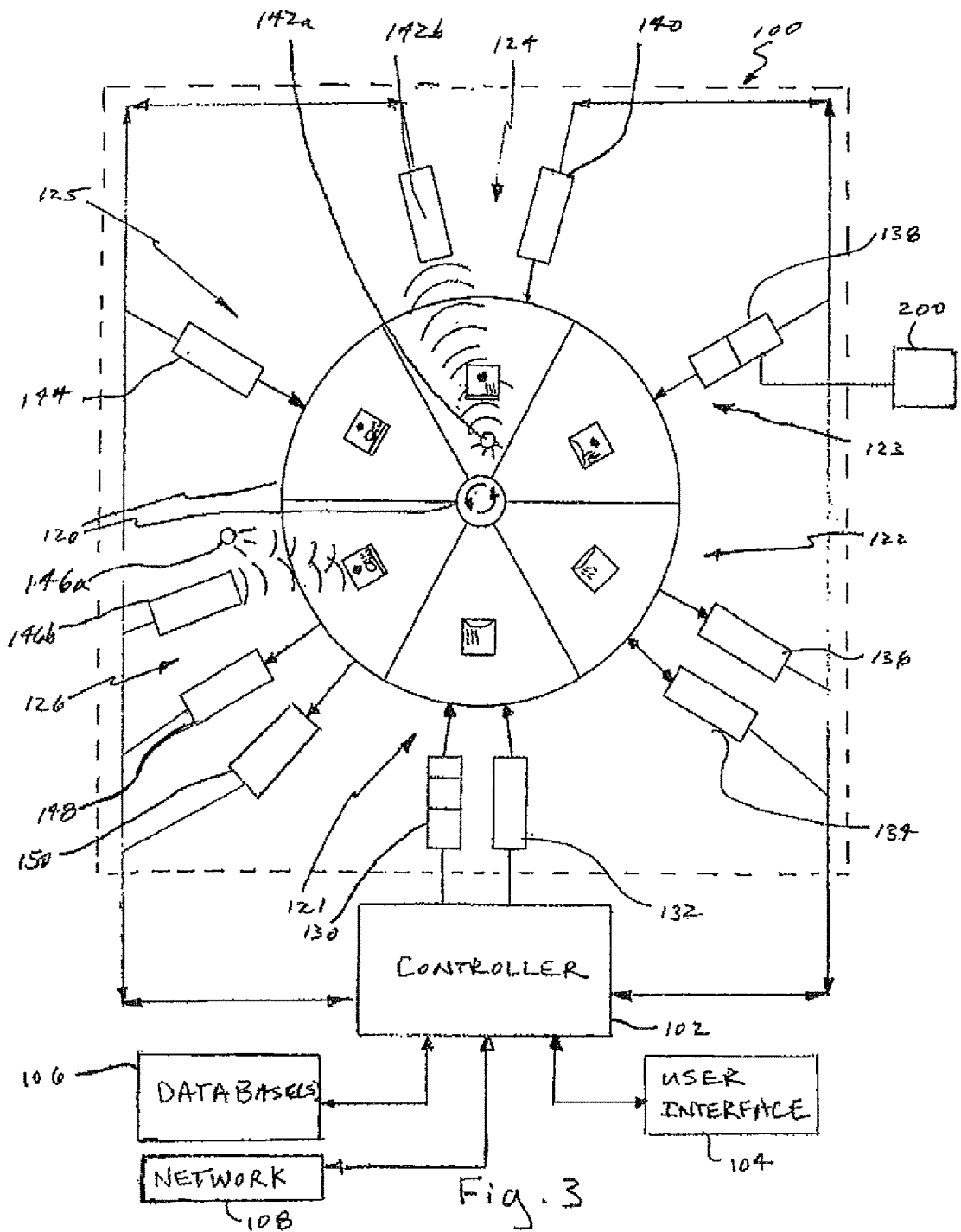
FIG. 3 is a schematic illustration of an automated system embodiment incorporating methodology of the embodiments corresponding with FIGS. 1 and 2.

Reference is now made to FIG. 3 which is a schematic illustration of componentry of an automated system embodiment incorporating methodology of the embodiments corresponding with FIG. 1 and FIG. 2 above. The system embodiment generally comprises an automated work center 100 operatively interconnected with a controller 102 (e.g., one or more computer microprocessors). The controller 102 may be operatively interconnected with a user interface 104, and one or more computer databases 106. User interface 104 may be employed to input and/or retrieve stored data from data base(s) 106 regarding one or more unit-dose medicament(s) to be packaged and inspected at automated work center 100, in accordance with signals provided by controller 102. Additionally, user interface 104 may be provided to output an alert signal to a user in connection with inspection operations and/or to allow a user to selectively view inspection images of a given receptacle. User interface 104 may include user input and display devices (e.g., a keyboard, point-and-click control device, a touch screen, etc.). Further, the controller 102 and/or database(s) 106 may be operatively interconnected to a network 108 of other controllers and/or databases for exchanging database information.

In relation to the automated work center 100, an automated, rotatable support platform 120 (e.g., in the form of a turntable) may be provided for supporting and rotatably advancing medicament receptacles through a plurality of work station locations, e.g. responsive to control signals provided by controller. In the illustrated embodiment, six automated work station locations are provided, wherein each of the work stations may be controlled by and otherwise operatively connected with controller 102.

A first work station location 121 may include a receptacle production device 130 and a receptacle printing device 132. The receptacle production device 130 may include a first portion for storing one or more reels of cylindrical plastic sleeve material, a second portion for cutting predetermined plastic sleeve length, and a third portion for defining a sealed bottom edge of an open port receptacle. The first portion, second portion and third portion may be adapted to automatically advance, cut, and seal the plastic sleeve material, respectively, pursuant to a control signal provided by controller 102. The printing device 132 may be operable for automatically printing data indicative of a corresponding given unit-dose medicament to be packaged within a given receptacle. The data may be printed directly on each given receptacle or upon a label applied to the receptacle. The printed data may include a machine-readable marking (e.g., a barcode) comprising identifying data corresponding with the given unit-dose medicament to be packaged.

After operation of receptacle production device 130 and receptacle printing device 132 at the first work station location 121, turntable 120 may be automatically rotated in response to a control signal from controller 102 to locate a given open port receptacle at a second work station location 122. A reader device 134 may be located at the second work station location 122 for automatic reading of machine-readable data printed on the receptacle. An output signal indicative of such (e.g., on a portion thereof) may be provided corresponding with the intended operation of printing device 132. The data read by the reader device 134 may be provided to be compared with the corresponding unit-dose medicament data at controller 102. In the event of a discrepancy (e.g., missing or inaccurate machine-readable data), the second work station location 122 may further include a discard device 136 for automatically removing the corresponding receptacle from the turntable 120 for disposal or other handling. In the event the accuracy of printed data on a given receptacle is verified, controller 102 may provide a control signal to affect rotation of turntable 120 so as to position the given receptacle at a third work station location 123.

An automated filler device 138 may be located at the third work station location 123 for automatically initiating a procedure for inserting a predetermined unit-dose medicament into a corresponding open port receptacle. By way of example, the automated filler device 138 may comprise a first portion that includes a tubular, straw-like device having a first end for receiving the unit-dose medicament and a second end advanceable for insertion into an open port receptacle for medicament delivery and retractable after insertion of the medicament. The automated filler device 138 may also include a second portion for staging the various unit-dose medicaments to be inserted. Optionally, the second portion may interface with a manually operated or automated input port 200.

Upon completion of an automated fill operation, controller 102 may provide a control signal so that the rotatable support platform 120 rotates to position the receptacle at a fourth work station location 124. An automated receptacle sealing device 140 may be located at the fourth work station location 124. The automated receptacle sealing device 140 may be operable to close and seal the open port of a given receptacle so as to define a sealably enclosed receptacle.

As shown in FIG. 3, an automated imaging device may also be located at the fourth work station location 124 for imaging the closed receptacle via an imaging signal. In this illustrated embodiment, the imaging device may include an imaging signal source 142a and an imaging signal detector 142b, wherein the imaging detection may obtain one or more images reflecting physical features corresponding with any contents of the receptacle. By way of example, a "backlight" arrangement may be provided by imaging signal source 142a and imaging signal detector 142b. In turn, any object(s) located within a receptacle, as well a shape and other physical features relating to such object(s) may be reflected by the image(s). In particular, the image(s) may reflect the number, size (e.g. as reflected by cross-dimensions, perimeter, area, etc.) and shape (e.g. pattern) of a medicament located within a receptacle. By way of example, such medicament may be in tablet form, caplet form, capsule form, manually-cut blister pack form, machine-cut blister pack form, or vial form. As may be appreciated, a digital image signal may be output by the imaging signal detector 142b for processing at controller 102.

In this regard, the controller 102 may process the digital image signal to extract image data utilizing preprogrammed software algorithms, e.g., as described above in relation to step 3 of the embodiment shown in FIG. 1. Further, the controller 102 may access database 106 to retrieve stored data and to compare such extracted image data with the stored data, as described above in relation to step 4a of the FIG. 1 embodiment. After image inspection of the contents of a given receptacle, the controller 102 may provide a control signal, wherein rotatable support platform 120 may rotate to a fifth work station 125. A receptacle production device 144 may be located at the fifth work station location 125 for automated performance of a predetermined production operation in relation to a given receptacle. By way of example, automated receptacle production device 144 may selectively form a sealed aperture in a given receptacle, e.g., wherein such aperture may be utilized for hanging of the corresponding receptacle on a hook, bar or the like subsequent to packaging and inspection. Thereafter, controller 102 may control rotatable support platform 120 to position a given receptacle at a sixth work station location 126.

As shown in FIG. 3, an automated imaging device may be located at the sixth work station location 126 for imaging the closed receptacle via an imaging signal. In one embodiment, the imaging device may include an imaging signal source 146a and an imaging signal detector 146b, wherein the imaging camera may obtain one or more images reflecting physical features of the receptacle. By way of example, an imaging signal source 146a and an imaging signal detector 146b (e.g., a camera) may be located on a common side of the sixth work station location 126, wherein a front-light image of a receptacle may be obtained. The image(s) may reflect physical attributes of a receptacle, including for example the configuration of the periphery of the receptacle (e.g., as defined at work station 121) and/or any aperture formed through the receptacle (e.g., as defined at work station 125).

The above description of the imaging steps performed at the fourth and sixth work station locations, 124, 126, respectively, are not necessarily limited to only obtaining physical features corresponding with any contents of the receptacle at the fourth work station location 124, and to only obtaining physical features of the receptacle itself at the sixth work station location 126. It is instead to be generally understood that the physical features of the receptacle and the physical features of any contents thereof can be obtained, either fully or partially, at any work station location which is equipped with an imaging device, e.g. at the fourth and sixth work station locations 124, 126, depending on the specific physical features of the receptacle and any content thereof which are most conveniently imaged with a "backlight", frontlight or any other arrangement of light and or camera which is desired, implemented and rendered available at a specific work station. For example, a different arrangement of imaging device can be provided for at the fourth work station location 124, where a backlight is obtained by a light source located outside the work station location 124, the mirrored image being reflected by a mirror located inside the work station location 124, opposite to the receptacle with respect to the light source, in order to reflect back the image outside the work station location 124 towards a camera. This configuration is mostly useful for the imaging of receptacles containing e.g. vials, while the imaging of receptacles containing e.g. pills can be accomplished at the sixth work station location 126, together with the acquisition of the physical features of the receptacle itself.

As may be appreciated, a digital image signal may be the output by the imaging signal detector 146b for processing at controller 102. In this regard, the controller 102 may process the digital image signal to extract image data utilizing preprogrammed software algorithms, e.g., as described above in relation to step 3 of the embodiment shown in FIG. 1. Further, the controller 102 may access database 106 to retrieve stored data and to compare such extracted image data with the stored data, as described above in relation to step 4b of the FIG. 1 embodiment. After image inspection of the physical attribute of a given receptacle, the controller 102 may provide a control signal wherein the rotatable support platform 120 may rotate to sixth work station 126.

In the event that an inspection comparison at the fourth work station location 124 and/or at sixth work station location 126 is failed, a removal device 148 may be provided at the sixth work station location 126 for automated discarding of the receptacle. By way of example, or automated chute or other similar device may be employed.

As further illustrated in FIG. 3, for receptacles that pass the inspection comparisons completed at the fourth and sixth work station locations 124, 126, such receptacles may be automatically advanced out of the automated work center 100 by a receptacle handling device 150 for storage and/or routing to a given patient. For example, handling device 150 may be provided for transporting receptacles to a temporary storage unit at which receptacles are suspended utilizing apertures formed at fifth work station 125.

Figure 4:
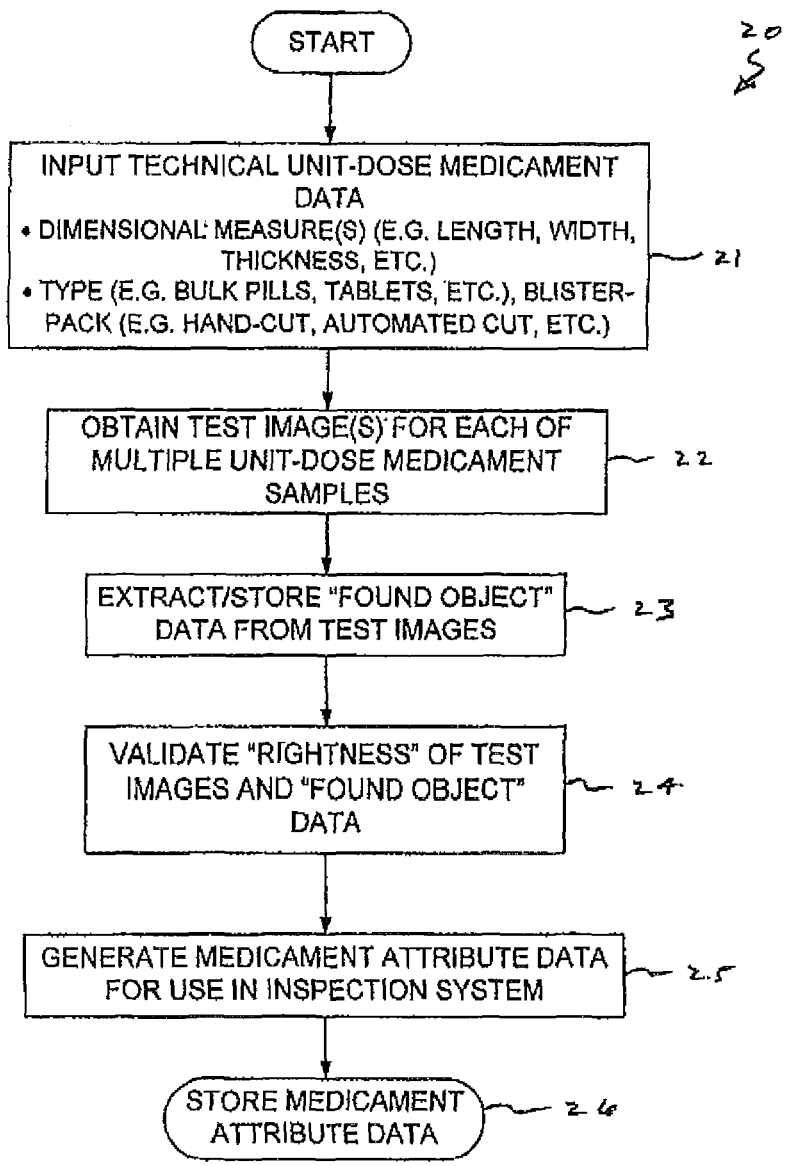
FIG. 4 illustrates a process embodiment for providing stored medicament attribute data employable in the embodiments of FIGS. 1-3.

Reference is now made to FIG. 4 which illustrates a process embodiment 20 for the establishment of predetermined unit-dose medicament attribute data employable step for 4 of the embodiment of FIG. 1 and in conjunction with the inspection of receptacles at the fourth work station 124 of the embodiment shown in FIG. 3 hereinabove. As may be appreciated, the obtainment of medicament attribute data may occur upon the introduction of a given unit-dose medicament intended for dispensation in a given inspection system.

As illustrated in FIG. 4, technical unit-dose medicament data may be initially input (step 21) into a computer database (e.g. at a user interface 104). Such input may be completed manually (e.g. at a user interface 104) and/or in an automated fashion. Automated input may be realized by accessing another database (e.g. via network 108) comprising input data and/or by extracting/storing/accessing data from one or more images of the given unit-dose medicament known to be of appropriate configuration and condition. The input technical data may include data relating to dimensional, or size, measures for the given unit-dose medicament (e.g., length, width, thickness, perimeter, area, etc.) and/or data relating to the type of the given unit-dose medicament (e.g., pills, tablets, blister-pack, hand-cut or automated-cut).

After technical data input, one or more test image(s) may be obtained for each one of multiple samples corresponding with the given unit-dose medicament (step 22). By way of example, the image(s) may be obtained utilizing image capture components such as those employed in the automated system of FIG. 3. Next, image data corresponding with the test image(s) for each of the samples may be processed to extract and store object data corresponding with any object(s) found in each given test image(s) (step 23). For example, digital image data may be processed by a processor using software comprising blob detection algorithms. The test image(s) obtained for each sample and/or the corresponding test image object data may be validated automatically and/or at least partially manually by determining whether each of the given unit-dose medicament samples is in fact of an acceptable nature and condition for dispensation (step 24). Process embodiments for such validation will be discussed in relation to FIGS. 5A and 5B hereinbelow. As illustrated in FIG. 4, validated test image object data and corresponding images may be employed to generate the medicament attribute data employable in the various embodiments described above (step 25). For example, the validated data and image(s) for a given collection of samples of a given unit-dose medicament may be statistically analyzed and/or comparatively analyzed to identify acceptable parameter measures and/or object patterns, as well as acceptable ranges relating thereto. In turn, the medicament attribute data may be stored in a database 106 (step 26) for use in an inspection systems (e.g., the automated system of FIG. 3).

Figure 5A:
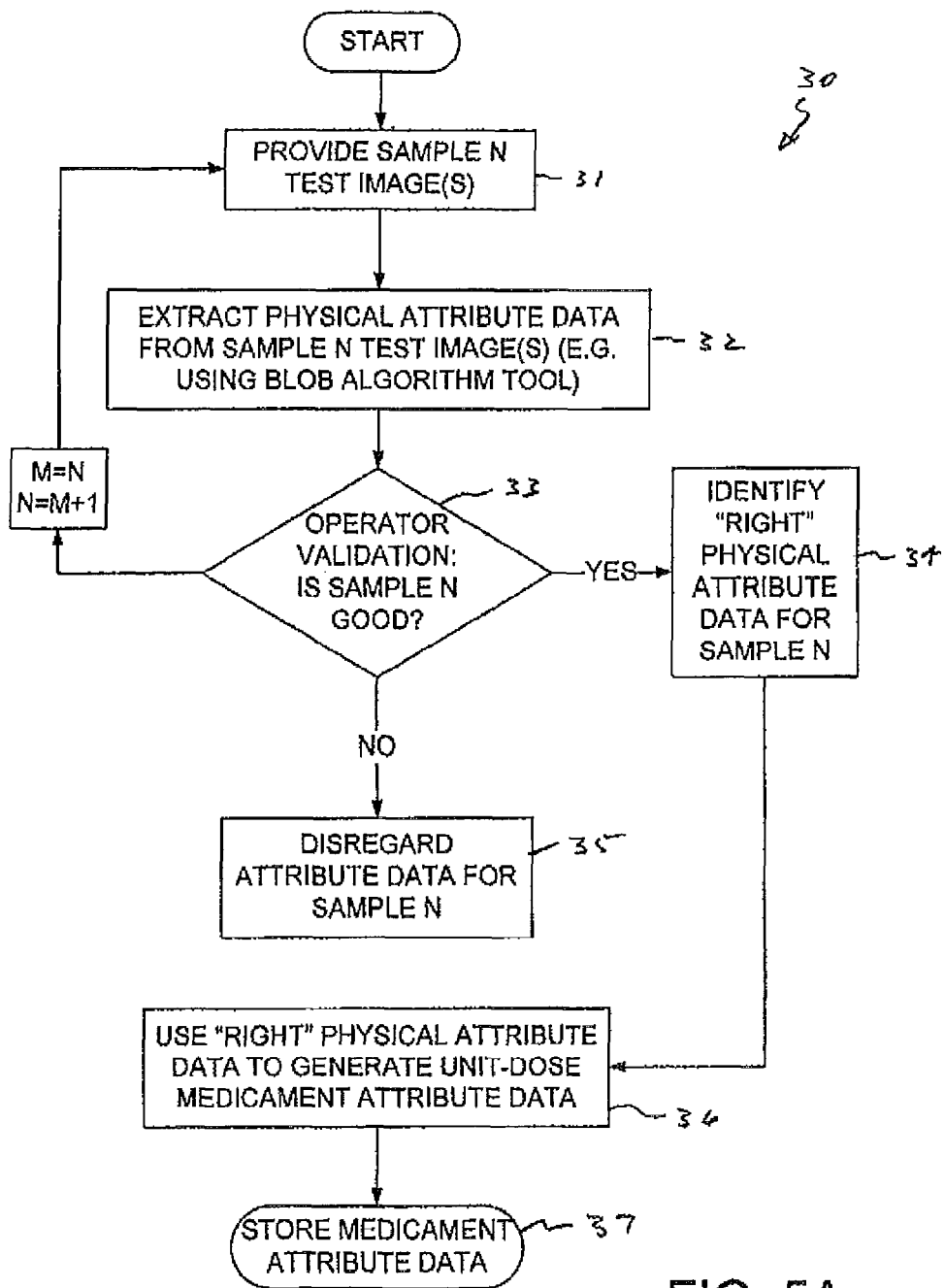
FIGS. 5A and 5B illustrate embodiments for validating data for use in the generation of medicament attribute data employable in the embodiments of FIGS. 1 and 3.

Reference is now made to FIG. 5A which illustrates one embodiment 30 for validating test images and corresponding data in generating medicament attribute data as referenced in relation to steps 24, 25 of the embodiment of FIG. 4. As shown, one or more test image(s) and/or corresponding test image object data may be provided for a given sample (step 31), and physical attribute data may be extracted from such test image(s) and/or corresponding test image object data (step 32). Such data extraction may be completed by a processor utilizing a blob software algorithm tool. By way of example, the physical attribute data may include data corresponding with a length, width, thickness area, perimeter or other physical measure, and optionally data obtained by use of the extracted data together with the initial input technical data corresponding with the given unit-dose medicament.

Next, a given sample may be inspected manually and/or in an automated manner (e.g. utilizing one or more software algorithms) to determine whether the sample is of an acceptable nature and condition (step 33). By way of example, an operator may visually inspect the actual sample and/or corresponding test image(s) to assess the physical size, condition, etc. of the sample.

To the extent the given sample is determined to be acceptable, the corresponding "acceptable", or "right" physical attribute data for the given sample may be identified for use in generating corresponding unit-dose medicament attribute data (step 34). For samples deemed not acceptable, the corresponding physical attribute data may be disregarded (step 35).

As shown in FIG. 5A, the process may be repeated for each one of a predetermined plurality of samples corresponding with a given unit-dose medicament. Upon completion of the process for each of the samples, the physical attribute data corresponding with each of the acceptable samples may be employed to generate unit-dose medicament attribute data employable in an overall production and inspection system (step 36). By way of example, the physical attribute data corresponding with the acceptable samples may be statistically analyzed to establish a range of values corresponding with each one of a plurality physical parameters corresponding with the given unit-dose medicament.

As shown in FIG. 5A, the medicament attribute data generated at step 36 may be stored for subsequent use in an inspection system (step 37). Such data may also be stored for subsequent refinement and/or access by another networked database.

Figure 5B:
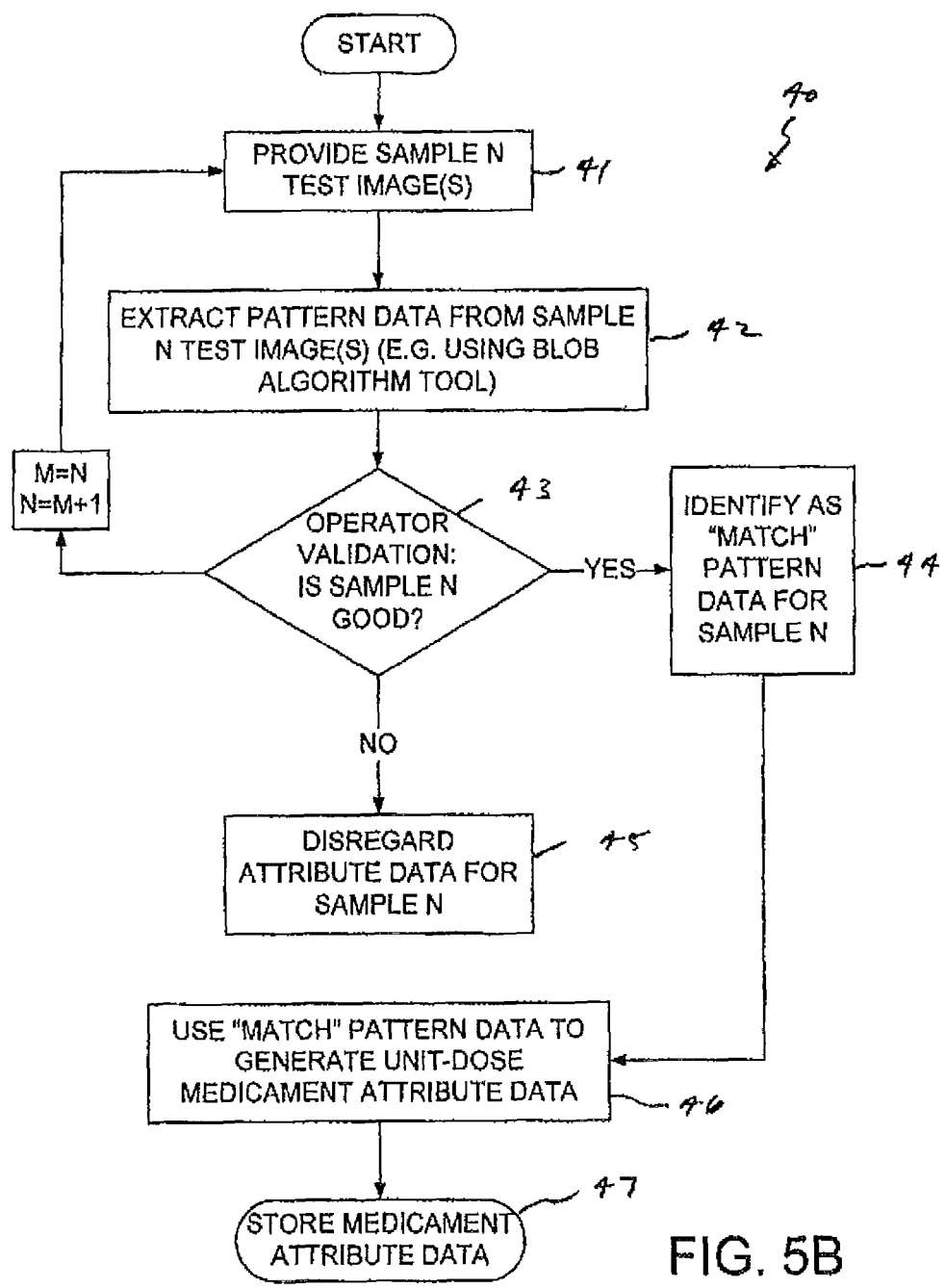

Reference is now made to FIG. 5B which illustrates one embodiment 40 for validating test images and corresponding data in generating medicament attribute data as referenced in relation to steps 24, 25 of the embodiment of FIG. 4. As shown, one or more test image(s) and/or corresponding test image object data may be provided for a given sample (step 41), and pattern attribute data may be extracted from such test image(s) and/or corresponding test image object data (step 42). By way of example, such data extraction may be completed by a processor utilizing a blob software algorithm tool. By way of example, the pattern attribute data may include data corresponding with a shape configuration or other pattern measure, and optionally data obtained by use of the extracted pattern data together with the initial input technical data corresponding with the given unit-dose medicament.

Next, a given sample may be inspected manually and/or in an automated manner (e.g. utilizing one or more software algorithms) to determine whether the sample is of an acceptable nature and condition (step 43). By way of example, the operator may visually inspect the actual sample and/or corresponding test image(s) to assess the pattern size, condition, etc. of the sample.

To the extent the given sample is determined to be acceptable, the corresponding "acceptable", or "right" pattern attribute data for the given sample may be identified for use in generating corresponding unit-dose medicament attribute data (step 44). For samples deemed not acceptable, the corresponding pattern attribute data may be disregarded (step 45).

As shown in FIG. 5B, the process may be repeated for each one of a predetermined plurality of samples corresponding with a given unit-dose medicament. Upon completion of the process for each of the samples, the pattern attribute data corresponding with each of the acceptable samples may be employed to generate unit-dose medicament attribute data employable in an overall production and inspection system (step 46). In this regard, one or more plurality of acceptable patterns, or configuration, may comprise the unit-dose medicament attribute data. Further, and by way of example, the pattern attribute data corresponding with the acceptable samples may be analyzed to establish a range of acceptable patterns or configurations.

As shown in FIG. 5B, the medicament attribute data generated at step 46 may be stored for subsequent use in an inspection system (step 47). Such data may also be stored for subsequent refinement and/or access by another networked database.

Example 1

FIGS. 6A-6D illustrate images of a type obtainable utilizing inspection processes and apparatus in various embodiments of the present invention. In each of FIGS. 6A-6D, a "back-light" approach has been utilized to obtain images of corresponding receptacles, e.g. receptacles imaged/inspected after a filling operation and closure of the given receptacle.

Figure 6A:
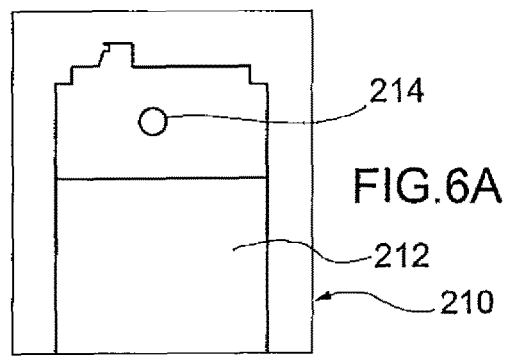
FIGS. 6A, 6B, 6C and 6D illustrate images obtainable for inspection use in various embodiments.

FIG. 6A illustrates an exemplary image 210 of a given receptacle 212 having an object 214 located therewithin. As will be further described hereinbelow, image 210 further illustrates an outline of a size and configuration corresponding with the predetermined unit-dose medicament intended for insertion into receptacle 212 during filling. In the FIG. 6A example, object 214 may be determined to be of appropriate size and configuration, thereby indicating acceptable presence of the intended unit-dose medicament.

Figure 6B:
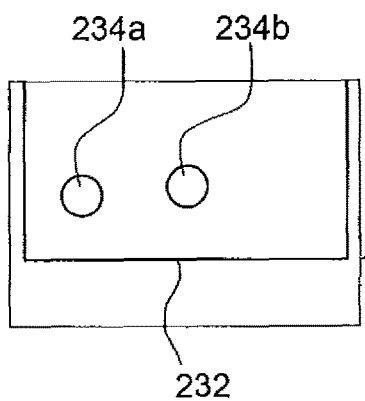

FIG. 6B illustrates an image 220 of a given receptacle 222. As shown, receptacle 222 fails to have any contents therewithin, i.e. no objects corresponding with a unit-dose medicament. In turn, image 220 may be utilized in the inspection process to identify a non-compliant receptacle 222, i.e. a receptacle in which a corresponding unit-dose medicament failed to be located therewithin during filling. In turn, receptacle may be discarded.

Figure 6C:
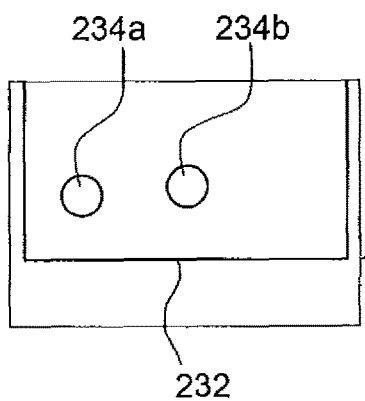

FIG. 6C illustrates an image 230 of a given receptacle 232 having multiple objects 234a, 234b located therewithin. In this case, if the corresponding predetermined unit-dose medicament for receptacle 232 was to have included a single object, e.g., a single unit-dose medicament (e.g., one pill, table etc.), then image 230 may indicate a non-compliant receptacle 232, i.e. a receptacle misfilled to include the incorrect unit-dose medicament. In turn, receptacle 232 may be discarded.

Figure 6D:
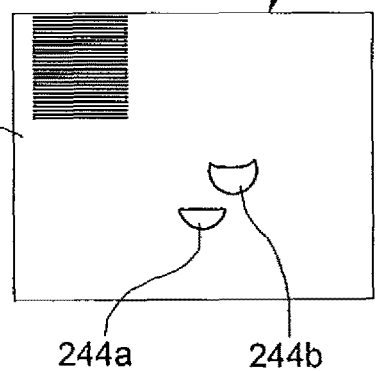

FIG. 6D illustrates an image 240 of a given receptacle 242 having objects 244a and 244b located therewithin. Objects 244a and 244b may be of a size and configuration that corresponds with a fractured unit-dose medicament. In such a case, receptacle 242 may be determined to be non-compliant, e.g., containing a damaged, corresponding unit-dose medicament.

Example 2

FIGS. 7A-7C illustrate various images of a type obtainable utilizing inspection processes and apparatus in various embodiments of the present invention. In each of FIGS. 7A-7C, a "back-light" approach has been utilized to obtain images of corresponding receptacles, e.g. receptacles imaged/inspected after a filling operation and closure of the given receptacle. The images reflect unit-dose medicaments of different sizes and shapes that may be inspected in various embodiments of the present invention.

FIG. 7A illustrates an image 250 of a given receptacle 252 having a medicament 254 with a circular periphery in one view. FIG. 7B illustrates an image 260 of given receptacle 262 containing a medicament with an elongate, tablet-like periphery. FIG. 7C illustrates an image 270 of a given receptacle 272 containing a medicament with a circular periphery in one view, such circular periphery being of a size that is smaller and therefore distinguishable from the circular periphery size shown by the image 250 in FIG. 7A.

Example 3

FIGS. 8A-8D illustrate images of a type obtainable utilizing inspection processes and apparatus in various embodiments of the present invention. In each of FIGS. 8A-8D, a "back-light" approach has been utilized to obtain images of corresponding receptacles, e.g., receptacles imaged/inspected after the filling operation and closure of the given receptacle. In each of FIGS. 8A-8D, outlines are shown superimposed on the corresponding images, and reflect how the size and configuration of contained objects may be compared with stored data corresponding with a predetermined unit-dose medicament that was to have been located in a given receptacle during filling. In each of the cases illustrated by FIGS. 8A-8D, the superimposed outlines correspond with a size and configuration for the intended contents, thereby reflecting corresponding packages that have been filled accurately.

In FIG. 8A, image 280 shows a given receptacle 282 having a rectangular object 284 located therein (e.g. a blister-pack), and a superimposed outline 286 corresponding with the configuration of the intended predetermined unit-dose medicament to have been located within receptacle 282 during filling operations. In FIG. 8B, image 290 shows a given receptacle 292 having a circular object 294 located therein, and a superimposed outline 296 corresponding with the intended predetermined unit-dose medicament to have been located within receptacle 292 during filling operations. In FIG. 8C, image 300 shows a given receptacle 302 having an oblong or tablet-shaped object 304 located therein, and a superimposed outline 306 corresponding with the intended predetermined unit-dose medicament to have been located within receptacle 302 during filling operations.

FIG. 8D shows an image 310 of a given receptacle 312 having an object 314 located therein and a superimposed outline 316. In this case, the object 314 may correspond with a unit-dose medicament comprising a vial, bottle, or other container for holding a liquid medicament. As shown in FIG. 8D, the superimposed outline 316 may comprise gradations that may be employed to analyze the object 314. The superimposed outlines may be automatically generated by imaging software to provide evidence to a user as to the shape, the score and/or the number of objects.

Figure 9:
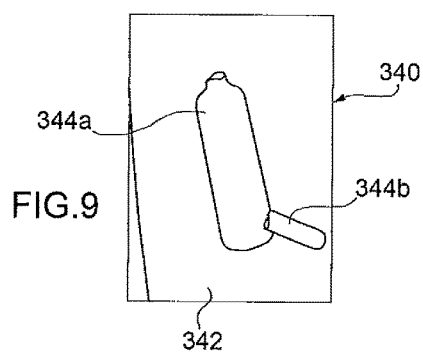
FIG. 9 illustrates another image obtainable for inspection use in various embodiments.

In this regard, FIG. 9 shows an image 340 of a given receptacle 342 having multiple objects 344a and 344b. In this case, objects 344a and 344b may correspond with broken portions of a receptacle intended for containment of a unit-dose medicament, e.g., a receptacle as per the object 314 of FIG. 8D noted above. As may be appreciated, the objects 344a, 344b of image 340 may yield corresponding extracted image data employable to determine that the corresponding liquid drug container is non-compliant due to the presence of objects 344a, 344b that do not correspond with the intended size and configuration of the intended unit-dose medicament (i.e. the liquid drug container).

Example 4

Figure 10B:
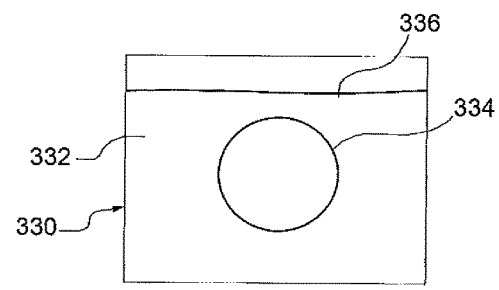
FIGS. 10A and 10B illustrate additional images obtainable for inspection use in various embodiments.
Figure 10A:
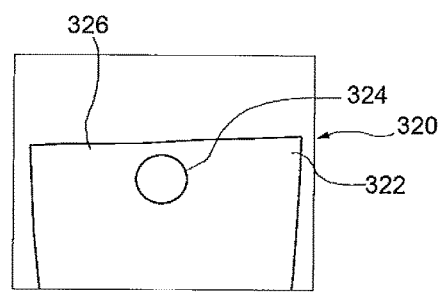

FIGS. 10A and 10B illustrate images of a type obtainable utilizing inspection processes and apparatus in various embodiments of the present invention. In each of FIGS. 10A and 10B, a "back-light" approach has been utilized to obtain images of corresponding receptacles, e.g. receptacles imaged/inspected after closure and one or more production operations for the given receptacle. In the illustrated images, the production operations may correspond with the provision of an edge seal and/or the provision of an aperture through a portion of the given receptacle.

FIG. 10A illustrates an image 320 of a portion of a receptacle 322 having an aperture 324 and an edge portion 326. The aperture 324 may correspond with a production operation formed for purposes of subsequent handling of the receptacle 322 (e.g., for hanging storage of the receptacle). Similarly, the side edge portion 326 may correspond with a production operation for establishing or sealing the edge portion 326 of receptacle 322. The size and configuration of the aperture 324 and/or edge portion 326 may be reflected by corresponding, extracted image data and compared with stored data reflecting the corresponding intended size and configuration of such features for the given receptacle. By way of example, FIG. 10A may illustrate that the given receptacle 322 is in compliance with receptacle-related parameters intended for containment of the corresponding unit-dose medicament.

FIG. 10B illustrates an image 330 of a portion of a receptacle 332 having an aperture 334 and an edge portion 336. The aperture 334 may correspond with a production operation formed for purposes of subsequent handling of the receptacle 332 (e.g. for hanging storage of the receptacle). Similarly, the side edge portion 336 may correspond with a production operation for establishing or sealing the edge portion 336 of receptacle 332. The size and configuration of the aperture 334 and/or edge portion 336 may be reflected by corresponding, extracted image data and compared with stored data reflecting the corresponding intended size and configuration of such features for the given receptacle. By way of example, FIG. 10A may illustrate that the given receptacle 332 is not in compliance with receptacle-related parameters intended for containment of the corresponding unit-dose medicament.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

We claim:

1. A method for use in handling a plurality of receptacles containing ones of a plurality of unit-dose medicaments, comprising:
   obtaining at least one image of each one of said plurality of receptacles;
   processing said at least one image of each one of said plurality of receptacles to extract corresponding image data;
   comparing said corresponding image data for each one of said plurality of receptacles to corresponding stored data;
   generating said stored data corresponding with at least one predetermined attribute of each one of said plurality of unit-dose medicaments for use in said comparing step; and
   discarding the each one of said plurality of receptacles if the comparing indicates that said corresponding image data exceeds a predetermined acceptance range of the corresponding stored data,
   wherein the step of obtaining at least one image further includes:
      first obtaining at least a first image using a first imaging device; and
      second obtaining at least a second image using a second imaging device,
      wherein the first obtaining step and the second obtaining step are completed at different locations,
   wherein the comparing step further includes:
      first comparing said corresponding image data to stored data corresponding with at least one predetermined attribute of said corresponding one of said plurality of unit-dose medicaments; and
      second comparing said corresponding image data to stored data corresponding with at least one predetermined attribute of said corresponding one of said plurality of receptacles, and
   wherein for each one of said plurality of unit-dose medicaments the generating step includes:
      obtaining at least a test image of each of a plurality of test samples corresponding to said one of said plurality of unit-dose medicaments;

extracting test image data from each said test image for each of said plurality of test samples;

inspecting said plurality of test samples in one of: an automated manner using at least one software algorithm, manual manner, and a partially automated and partially manual manner, to identify acceptable ones of said test samples; and only if a said test sample is acceptable, then using said test image data corresponding with said acceptable ones of said plurality of test samples to generate said stored data corresponding with said one of said plurality of unit-dose medicaments, and if a said test sample is not acceptable, then disregarding said test image data corresponding with the unacceptable test sample, wherein for each one of said plurality of unit-dose medicaments said using said test image data step comprises:

performing statistical analyses of said test image data corresponding with said acceptable ones of said plurality of test samples to establish a corresponding acceptance range for use in said comparing step.

2. The method as recited in claim 1, further comprising: sealably closing said plurality of receptacles, wherein for each one of said plurality of receptacles said sealably closing step is completed prior to said step of obtaining at least one image.

3. The method as recited in claim 1, wherein for each one of said plurality of receptacles said step of obtaining at least one image comprises:

illuminating one side of said one of said plurality of receptacles; and capturing said at least one image on another side of said one of said plurality of receptacles during at least a portion of said illuminating step.

4. The method as recited in claim 1, wherein for each one of said plurality of receptacles said corresponding image data comprises at least one of a contents-related group consisting of:

data relating to a presence of an object within said one of said plurality of receptacles;

data relating to a number of objects within said one of said plurality of receptacles;

data relating to a shape of an object within said one of said plurality of receptacles; and data relating to a size of an object within said one of said plurality of receptacles.

5. The method as recited in claim 4, wherein said at least one predetermined attribute of said corresponding one of said plurality of unit-dose medicaments is one of a first predetermined group consisting of:

a predetermined number of physically discrete units comprising said corresponding one of said plurality of unit-dose medicaments;

a predetermined shape of each physically discrete unit comprising said corresponding one of said plurality of unit-dose medicaments; and a predetermined size of each physically discrete unit comprising said corresponding one of said plurality of unit-dose medicaments.

6. The method as recited in claim 5, wherein for each one of said plurality of receptacles said corresponding image data comprises at least one of a receptacle-related group consisting of:

data relating to a shape of a predetermined sealed region of said one of said plurality of receptacles;

data relating to a shape of a predetermined edge portion of said one of said plurality of receptacles; and data relating to a light transmissivity of a predetermined region of said one of said plurality of receptacles.

7. The method as recited in claim 6, wherein said at least one predetermined attribute of said corresponding one of said plurality of receptacles is one of a second predetermined group consisting of:

a predetermined shape of said predetermined sealed region of said one of said plurality of receptacles;

a predetermined shape of said predetermined edge portion of said one of said plurality of receptacles; and a predetermined light transmissivity of said predetermined region of said one of said plurality of receptacles.

8. The method as recited in claim 1, further comprising: separately locating each of said plurality of receptacles at a predetermined fill location for intended receipt of said corresponding one of said plurality of unit-dose medicaments, said locating step being completed before said step of obtaining at least one image.

9. The method as recited in claim 8, wherein for each one of said plurality of receptacles said locating step comprises:

initiating a fill operation to insert said corresponding one of said plurality of unit-dose medicaments into corresponding one of said plurality of receptacles.

10. The method as recited in claim 9, further comprising: separately closing each of said plurality of receptacles, wherein for each one of said plurality of receptacles the closing step is completed after said locating step and prior to said step of obtaining at least one image.

11. The method as recited in claim 10, wherein said closing step is completed at a predetermined closure location.

12. The method as recited in claim 11, wherein said step of obtaining at least one image is completed at said predetermined closure location.

13. The method as recited in claim 12, further comprising:

providing a machine-readable marking on each of said plurality of receptacles, wherein for each one of said plurality of receptacles a corresponding machine-readable marking comprises data relating to said corresponding one of said plurality of unit-dose medicaments;

verifying the presence and accuracy of the corresponding machine-readable marking for each of said plurality of receptacles, wherein any of said plurality of receptacles that is not verified is identified as non-verified; and removing any non-verified receptacles.

14. The method as recited in claim 13, wherein each of said steps of obtaining at least one image, processing, comparing, discarding, locating, initiating, closing, providing, verifying and removing steps is at least partially automated.

15. The method as recited in claim 1, further comprising:

collecting said corresponding image data and comparison data resulting from said comparing step to generate historical data; and utilizing said historical data to modify said stored data.

16. The method as recited in claim 1, further comprising:

storing said stored data in a database at a facility where a medicament dispensary is located; and providing data from a remote database to modify said stored data, wherein said remote database comprises data collected from a plurality of medicament dispensaries employing said method.

17. The method as recited in claim 1, wherein for each one of said plurality of unit-dose medicaments said stored data comprises pattern data indicative of at least one acceptable shape for said one of said plurality of unit-dose medicaments.

18. The method as recited in claim 1, wherein for each one of said plurality of unit-dose medicaments said stored data comprises pattern data indicative of a plurality of acceptable shapes for said one of said plurality of unit-dose medicaments.

19. The method as recited in claim 1, wherein for each one of said plurality of unit-dose medicaments said stored data comprises physical attribute data indicative of at least one acceptable physical measure for said one of said plurality of unit-dose medicaments.

20. The method as recited in claim 1, wherein for each one of said plurality of unit-dose medicaments said stored data comprises physical attribute data indicative of a plurality of acceptable physical measures for said one of said plurality of unit-dose medicaments.

21. The method as recited in claim 1, wherein said step of generating said stored data is carried out prior to said step of comparing.

* * * * *